United States Patent
Wang et al.

(10) Patent No.: US 11,779,490 B1
(45) Date of Patent: Oct. 10, 2023

(54) MINIMALLY INVASIVE AB INTERNO TRIPLE SURGERY FOR OPEN-ANGLE GLAUCOMA

(71) Applicant: Beijing Institute of Ophthalmology, Beijing Tongren Hospital, Capital Medical University, Beijing (CN)

(72) Inventors: Ningli Wang, Beijing (CN); Qing Sang, Beijing (CN); Jin Wang, Beijing (CN); Dapeng Mu, Beijing (CN); Xueting Pei, Beijing (CN); Diya Yang, Beijing (CN)

(73) Assignee: Beijing Institute of Ophthalmology, Beijing Tongren Hospital, Capital Medical University, Beijing (CN)

( * ) Notice: Subject to any disclaimer, the term of this patent is extended or adjusted under 35 U.S.C. 154(b) by 0 days.

(21) Appl. No.: 18/045,622

(22) Filed: Oct. 11, 2022

(51) Int. Cl.
| | |
|---|---|
| *A61F 9/007* | (2006.01) |
| *A61F 9/008* | (2006.01) |
| *A61F 9/00* | (2006.01) |
| *A61B 17/04* | (2006.01) |
| *A61B 3/117* | (2006.01) |

(52) U.S. Cl.
CPC ........... *A61F 9/00781* (2013.01); *A61B 3/117* (2013.01); *A61B 17/0469* (2013.01); *A61F 9/00* (2013.01); *A61F 9/007* (2013.01); *A61F 9/0008* (2013.01); *A61F 9/00709* (2013.01); *A61F 9/00736* (2013.01); *A61F 2009/00868* (2013.01); *A61F 2009/00891* (2013.01); *A61M 2210/0612* (2013.01)

(58) Field of Classification Search
None
See application file for complete search history.

(56) References Cited

U.S. PATENT DOCUMENTS

| | | | | |
|---|---|---|---|---|
| 7,967,772 | B2 * | 6/2011 | McKenzie | A61M 5/31511 604/19 |
| 2012/0303010 | A1 * | 11/2012 | Vijfvinkel | A61F 9/00781 606/6 |
| 2016/0287438 | A1 * | 10/2016 | Badawi | A61K 31/728 |
| 2018/0147088 | A1 * | 5/2018 | Liang | A61B 17/0231 |

* cited by examiner

*Primary Examiner* — Javier G Blanco
(74) *Attorney, Agent, or Firm* — CBM PATENT CONSULTING, LLC

(57) ABSTRACT

A minimally invasive ab interno triple surgery for open-angle glaucoma comprises knotting and fixing a suture at the head end of an optical fiber catheter; performing miosis with carbachol, injecting the viscoelastic into the anterior chamber, making a lateral incision at the infratemporal corneal limbus, and placing the optical fiber catheter; cutting the Schlemm's canal on the nasal side of the anterior chamber, inserting an optical fiber into the incision on the Schlemm's canal, and cutting off the suture; injecting the viscoelastic to expand while retreating the microcatheter, and regularly injecting the viscoelastic; making a conjunctival flap on the eye and nose side, performing anterior chamber paracentesis, clamping out the suture using intraocular microforceps, and knotting in the sclera tunnel; and suturing the conjunctival flap using the suture, coating the eyes, and covering the eyes with gauze to finish the surgery.

1 Claim, 1 Drawing Sheet

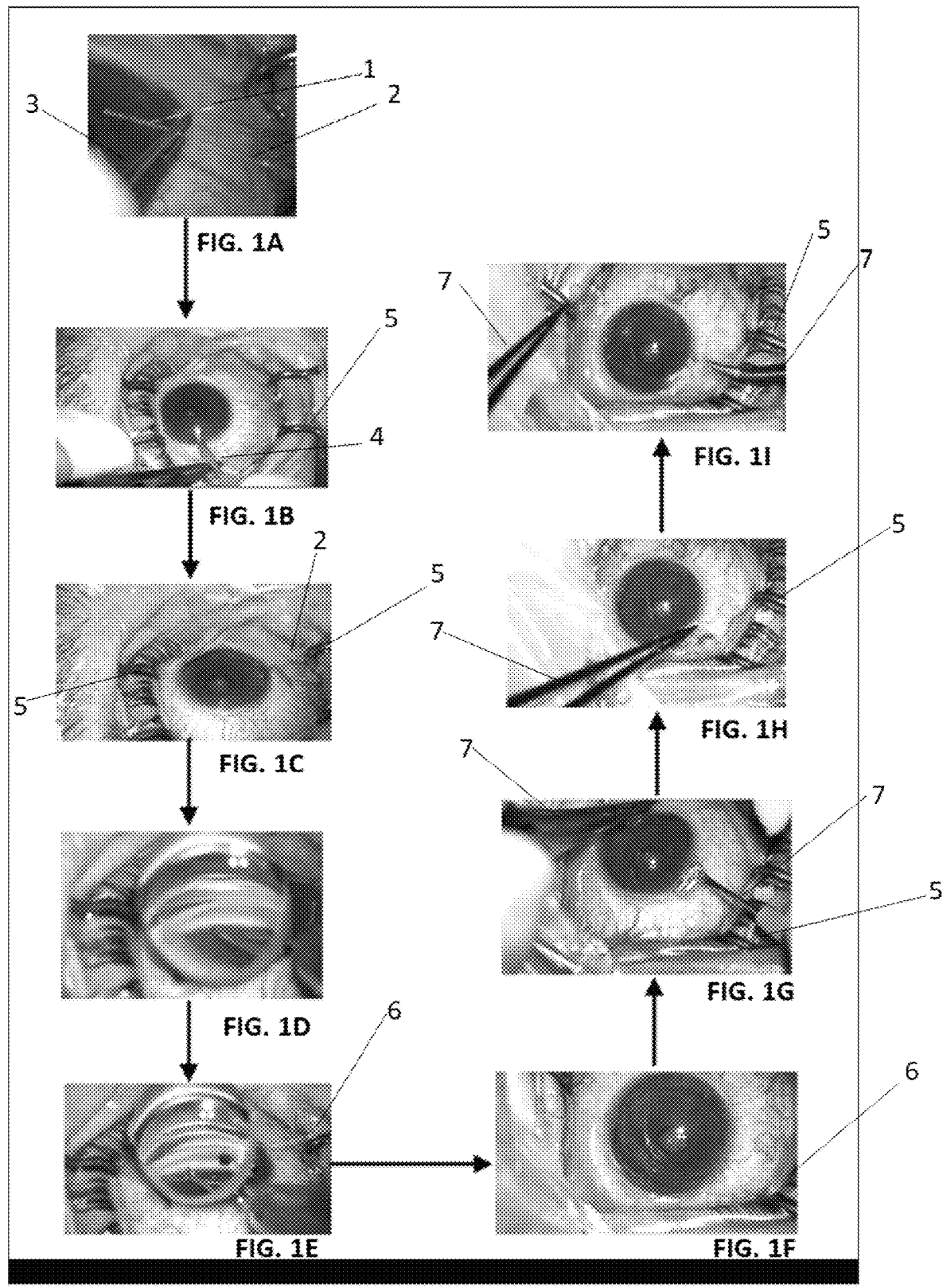

MINIMALLY INVASIVE AB INTERNO TRIPLE SURGERY FOR OPEN-ANGLE GLAUCOMA

TECHNICAL FIELD

The present invention relates to the technical field of disease treatment, specifically a minimally invasive ab interno triple surgery for open-angle glaucoma.

BACKGROUND ART

At present, the surgical methods for open-angle glaucoma commonly used in clinical practice include gonioscopy-assisted ab interno transluminal trabeculotomy, ab interno Schlemm's canal dilation, ab externo Schlemm's canaloplasty, trabeculotomy using a KDB, etc. Every surgery has its limitations. The ab interno transluminal trabeculotomy, which is most commonly applied clinically, is to remove the resistance at the trabecular meshwork by full-circumference trabeculotomy, which reduces the intraocular pressure, but damages the trabecular meshwork and leads to a high incidence of postoperative cyclodialysis. The ab externo Schlemm's canaloplasty is performed with the operative route of conjunctiva, with large trauma and failure to remove the resistance at the trabecular meshwork as its consequences.

SUMMARY OF THE PRESENT INVENTION

The objective of the present invention is to provide a minimally invasive ab interno triple surgery, characterized by definite effects, more minimally invasive and safer features, for the patients with open-angle glaucoma. With respect to the surgical mechanism design, partial trabeculotomy, Schlemm's canaloplasty and Schlemm's canal and collector channel dilatation can be all carried out, and an aqueous humor outflow channel is rebuilt to resolve at least one technical problem in the background art.

In order to achieve the above objective, the present invention is provided with the following technical solution:

The present invention provides a minimally invasive ab interno triple surgery for open-angle glaucoma. The surgery comprises the steps as follows:

Step 1: Knot and fix a 10-0 suture at the head end of the optical fiber catheter, and prepare the viscoelastic at the tail end of the optical fiber catheter in advance;

Step 2: After general anesthesia in the patient, make a corneal limbus incision at the temporal side of the patient using a #15 scalpel, perform miosis with carbachol, inject the viscoelastic into the anterior chamber, make a lateral incision at the infratemporal corneal limbus using the #15 scalpel, and place the optical fiber catheter into the incision;

Step 3: Under the direct vision of a gonioscope, cut the Schlemm's canal by about 2-3 mm on the nasal side of the anterior chamber using a membrane stripping hook, insert the optical fiber into the incision on the Schlemm's canal, and cut off the 10-0 suture at the head end of the optical fiber after moving clockwise by 360° underneath to separate the optical fiber from the 10-0 suture;

Step 4: Retreat the catheter slowly, perform expansion with the viscoelastic while retreating the catheter by 1-2 meshes at each clock point, and use a crystal positioning hook to assist in fixation during retreating the catheter to avoid cutting the trabecular meshwork until the catheter is completely retreated. Leave the 10-0 suture in the Schlemm's canal with the head and tail ends remained in the anterior chamber in a drift way, and mark the position where the 10-0 suture penetrates out of the Schlemm's canal on the surface of the conjunctiva with a marker;

Step 5: Make a conjunctival flap on the nasal side of the patient according to the mark by the marker, make a linear sclera tunnel at the sclera under the conjunctival flap with the depth of about 1 mm, perform anterior chamber paracentesis at the position where the 10-0 suture penetrates out using a 23-G paracentesis knife; hook out the free ends on both sides of the 10-0 suture using a microsurgery crochet hook, and knot on the surface of the sclera tunnel; and Step 6: Perform interrupted suture of the conjunctival flap using the 10-0 suture, apply TobraDex ophthalmic ointment to the eye, and cover the eye with gauze to finish the surgery.

Preferably, a corneal limbus incision is made on the temporal side of the patient using a #15 scalpel, miosis performed with carbachol, the viscoelastic injected into the anterior chamber, and a lateral incision made at the infratemporal corneal limbus using the #15 scalpel.

Preferably, the optical fiber is inserted into the incision on the Schlemm's canal and moves clockwise by 360° underneath.

Preferably, the position where the 10-0 suture penetrates out of the Schlemm's canal is marked on the surface of the conjunctiva using a marker.

Preferably, a conjunctival flap is made on the nasal side of the patient according to the mark by the marker, a linear sclera tunnel made at 1/2 to 1/3 of the sclera thickness with the depth of about 1 mm, anterior chamber paracentesis conducted at the position where the 10-0 suture penetrates out using a 23-G paracentesis knife, free ends on both sides of the 10-0 suture hooked out using a microsurgery crochet hook and knotting performed on the surface of the sclera tunnel.

The present invention has the beneficial effects as follows: the surgery is more minimally invasive; three mechanisms are adopted to reduce intraocular pressure; postoperative complications are few, which leads to a more favorable safety profile; both postoperative blood return at the collector channel and anterior chamber hyphema can be prevented; and cyclodialysis can also be prevented.

The additional advantages of the present invention will be highlighted in the following description, or acquired by practice of the present invention.

BRIEF DESCRIPTION OF THE DRAWINGS

In order to more clearly describe the technical solutions of the embodiments of the present invention, the accompanying drawings used in the description of the embodiments will be described briefly below. Obviously, the accompanying drawings in the following description are only some embodiments of the present invention, and for those with ordinary skill in the art, other drawings can also be obtained from these accompanying drawings without creative efforts.

The FIG. 1A-1I show a flowchart of a surgery in an embodiment of the present invention.

FIG. 1A depicts knotting and fixing a 10-0 suture at the head end of the optical fiber catheter;

FIG. 1B depicts making a corneal limbus incision at temporal side of a patient using a #15 scalpel, performing miosis with carbachol;

FIG. 1C depicts making a lateral incision;

FIG. 1D depicts cutting a Schlemm's canal by about 2-3 mm on nasal side of the anterior chamber using a membrane stripping hook, inserting the optical fiber into the incision on the Schlemm's canal, and cutting off 10-0 suture at the head end of the optical fiber after the head end of the optical fiber catheter is introduced into Schlemm's canal and slowly advanced by 360° to separate the optical fiber from the 10-0 suture under a direct vision of a gonioscope;

FIG. 1E depicts retreating the catheter slowly, use a crystal positioning hook to assist in fixation during retreating the catheter to avoid cutting the trabecular meshwork until the catheter is completely retreated;

FIG. 1F depicts leaving the 10-0 suture in the Schlemm's canal with the head and tail ends of 10-0 suture remained in the anterior chamber, and marking the position where the 10-0 suture penetrates out of the Schlemm's canal on surface of a conjunctiva with a marker;

FIG. 1G depicts performing anterior chamber paracentesis at the position where the 10-0 suture penetrates out using a 23-G paracentesis knife; hooking out free ends on both sides of the 10-0 suture using a microsurgery crochet hook, and knotting on the surface of the sclera tunnel;

FIG. 1H depicts performing anterior chamber paracentesis at the position where the 10-0 suture penetrates out using a 23-G paracentesis knife; hooking out free ends on both sides of the 10-0 suture using a microsurgery crochet hook, and knotting on the surface of the sclera tunnel;

FIG. 1I shows for performing interrupted suture of the conjunctival flap using the 10-0 suture, Clean the anterior chamber and complete the surgery.

Reference 1 indicates optical fiber catheter, 2 indicates 10-0 suture, 3 indicates micro tweezer, 4 indicates syringe, 5 indicates #15 scalpel, 6 indicates viscoinjector screw, and 7 indicates 23-G paracentesis knife.

DETAILED DESCRIPTION OF THE PRESENT INVENTION

The embodiments of the present invention will be described in detail below, the examples of which will be shown in the accompanying drawings, wherein the same or similar marks refer to the same or similar elements or elements having the same or similar functions throughout. The embodiments described below with the accompanying drawings are exemplary and are only used for explaining the present invention, but not to be considered as a limitation of the present invention.

It will be understood by those skilled in the art that, unless otherwise defined, all terms (including technical and scientific terms) used herein have the same meaning as commonly understood by those with ordinary skill in the art to which the present invention belongs.

It should also be understood that terms such as those defined in general dictionaries should be understood to have meanings consistent with the meanings in the context of the prior art and, unless defined as herein, these terms are not to be explained in an idealized or overly formal sense.

It will be understood by those skilled in the art that unless expressly stated otherwise, the singular forms "a", "an", "the" and "this" as used herein can include the plural forms as well. It should be further understood that the word "comprising" used in the specification for the present invention refers to the presence of characteristics, integers, steps, operations, elements and/or components, but does not exclude the presence or addition of one or more other characteristics, integers, steps, operations, elements and/or combinations thereof.

In the description of this specification, description with reference to the terms "one embodiment", "some embodiments", "example", "specific example", or "some examples", etc., refers to that the specific characteristics, structures, materials or features described based on the embodiment or example is included in at least one embodiment or example of the present invention. Furthermore, the specific characteristics, structures, materials or features described may be combined in any suitable manner in any one or more embodiments or examples. Furthermore, in case of not conflicting each other, those skilled in the art may connect and combine different embodiments or examples described in this specification, as well as the characteristics of the different embodiments or examples.

In order to facilitate the understanding of the present invention, the present invention will be further explained and described below with reference to the accompanying drawings with specific embodiments, and the specific embodiments do not constitute limitations on the embodiments of the present invention.

Those skilled in the art should understand that the accompanying drawings are only schematic diagrams of the embodiments, and the components therein are not necessary to implement the present invention.

EMBODIMENT

As shown in FIG. 1, the embodiment provided a minimally invasive ab interno triple surgery for open-angle glaucoma. The surgery comprised the steps as follows:

Step 1: A 10-0 suture was knotted and fixed at the head end of the optical fiber catheter, and the viscoelastic was prepared at the tail end of the optical fiber catheter in advance;

Step 2: After general anesthesia in the patient, a corneal limbus incision was made on the temporal side of the patient using a #15 scalpel, miosis performed with carbachol, the viscoelastic injected into the anterior chamber, a lateral incision made at the infratemporal corneal limbus using the #15 scalpel, and the optical fiber catheter placed into the incision;

Step 3: Under the direct vision of a gonioscope, the Schlemm's canal was cut by about 2-3 mm on the nasal side of the anterior chamber using a membrane stripping hook, the optical fiber inserted into the incision on the Schlemm's canal, and the 10-0 suture cut off at the head end of the optical fiber after moving clockwise by 360° underneath to separate the optical fiber from the 10-0 suture;

Step 4: The catheter was retreated slowly, expansion performed with the viscoelastic while the catheter was retreated by 1-2 meshes at each clock point, and a crystal positioning hook used to assist in fixation during the catheter was retreated to avoid cutting the trabecular meshwork until the catheter was completely retreated. The 10-0 suture was left in the Schlemm's canal with the head and tail ends remained in the anterior chamber in a drift way, and the position where the 10-0 suture penetrates out of the Schlemm's canal on the surface of the conjunctiva was marked with a marker;

Step 5: A conjunctival flap was made on the nasal side of the patient according to the mark by the marker, a linear sclera tunnel made at the sclera under the conjunctival flap with the depth of about 1 mm, anterior chamber paracentesis performed at the position where the 10-0 suture penetrated out using a 23-G paracentesis knife; the free ends hooked out on both sides of the 10-0 suture using a microsurgery crochet hook, and knotted on the surface of the sclera tunnel; and Step 6: Interrupted suture of the conjunctival flap was performed using the 10-0 suture, TobraDex ophthalmic ointment applied to the eye, and the eye covered with gauze to finish the surgery.

A corneal limbus incision was made on the temporal side of a patient using a #15 scalpel, miosis performed with carbachol, the viscoelastic injected into the anterior chamber, and a lateral incision made at the infratemporal corneal limbus of the patient using the #15 scalpel.

An optical fiber was inserted into the Schlemm's canal incision and moved clockwise by 360° underneath.

A position where the 10-0 suture penetrated out of the Schlemm's canal was marked on the surface of the conjunctiva with a marker.

A conjunctival flap was made on the eye and nose side of the patient according to the mark of the marking pen; a linear sclera tunnel was made at 1/2-1/3 of the sclera thickness, and the depth was about 1 mm; anterior chamber paracentesis was conducted at the position where the 10-0 suture penetrated out through a 23G paracentesis knife; and free ends on the two sides of the 10-0 suture were hooked out through a microsurgery crochet hook and were knotted on the surface of the sclera tunnel.

In conclusion, the surgical procedure in the embodiment of the present invention was a novel surgery to reduce intraocular pressure in open-angle glaucoma, which showed definite effects, more minimally invasive and safer features. The postoperative intraocular pressure reduction mechanism was described as follows: 1. During the surgery, the trabecular meshwork within a small range was cut open to serve as an inlet for aqueous humor drainage, and aqueous humor was drained into a Schlemm's canal, for which the resistance at the trabecular meshwork was reduced, and most of the reserved trabecular meshwork was not damaged. Schlemm's canaloplasty was performed with the 10-0 suture, for which permanent canaloplasty was realized, the resistance was reduced, and the expansion of the collector channel opening was performed with the viscoelastic.

This surgery was a unique surgical procedure simultaneously meeting the above three mechanisms. 2) The surgery was more minimally invasive and reserved most of the trabecular meshwork.

Compared with the prior art, the present invention had the advantages that 1) the surgery was more minimally invasive, and compared with the existing clinical surgeries, the surgery reserved the majority of the trabecular meshwork and did not cut all trabecular meshwork. And 2) Intraocular pressure was reduced through three mechanisms (the intraocular pressure could be reduced only through two mechanisms at most by the existing surgeries); and postoperative complications were few, which led to a more favorable safety profile. Because the majority of the trabecular meshwork was reserved, both the postoperative blood return at the collector channel and anterior chamber hyphema could be prevented. In addition, cyclodialysis could also be prevented.

Although the specific embodiments of the present invention were described above with reference to the accompanying drawings, they were not intended to limit the protection scope of the present invention, and it should be understood by those skilled in the art that, on the basis of the technical solutions disclosed in the present invention, various modifications or deformations that could be made by those skilled in the art without the need for creative work should all fall within the protection scope of the present invention.

What is claimed is:

1. A method of minimally invasive ab interno triple surgery for open-angle glaucoma, comprising the following steps:
   step 1: knotting and fixing a 10-0 suture at head end of optical fiber catheter, and preparing a viscoelastic at tail end of the optical fiber catheter;
   step 2: after general anesthesia in the patient, making a corneal limbus incision at temporal side of a patient using a #15 scalpel, performing miosis with carbachol, injecting the viscoelastic into anterior chamber of the eye, making a lateral incision at an infratemporal corneal limbus using the #15 scalpel, and placing the head end of the optical fiber catheter into the lateral incision;
   step 3: under a direct vision of a gonioscope, cutting a Schlemm's canal by about 2-3 mm on nasal side of the anterior chamber using a membrane stripping hook, inserting the optical fiber into the Schlemm's canal, and cutting off 10-0 suture at the head end of the optical fiber catheter after the head end of the optical fiber catheter is inserted into Schlemm's canal and slowly advanced clockwise by 360° to separate the optical fiber catheter from the 10-0 suture;
   step 4: retreating the catheter slowly while performing expansion with the viscoelastic as delivered in portions into the Schlemm's canal through a lumen of the optical fiber catheter, and using a crystal positioning hook to assist in fixation during retreating the catheter to avoid cutting the trabecular meshwork until the catheter is completely retreated; leaving the 10-0 suture in the Schlemm's canal with head and tail free ends of 10-0 suture penetrating out of the Schlemm's canal and into the anterior chamber, and marking the position where the 10-0 suture penetrates out of the Schlemm's canal on surface of a conjunctiva with a marker;
   step 5: making a conjunctival flap on the nasal side of the patient according to marked position, making a linear sclera tunnel at the sclera under the conjunctival flap with a depth of about 1 mm, performing anterior chamber paracentesis at the position where the 10-0 suture penetrates out using a 23-G paracentesis knife; hooking out free ends on both sides of the 10-0 suture using a microsurgery crochet hook, and knotting on the surface of the sclera tunnel; and
   step 6: performing interrupted suture of the conjunctival flap using the 10-0 suture, applying TobraDex ophthalmic ointment to the eye, and covering the eye with gauze to finish the surgery.

* * * * *